United States Patent [19]

Smith

[11] Patent Number: 4,844,818

[45] Date of Patent: Jul. 4, 1989

[54] METHOD FOR SEPARATING THE CELLULAR COMPONENTS OF BLOOD SAMPLES

[75] Inventor: Ward C. Smith, Mahwah, N.J.

[73] Assignee: Becton Dickinson & Company, Franklin Lakes, N.J.

[21] Appl. No.: 112,721

[22] Filed: Oct. 23, 1987

[51] Int. Cl.$^4$ .............................................. B01D 21/26
[52] U.S. Cl. .................................. 210/789; 210/516; 422/101; 436/177; 494/16; 494/37
[58] Field of Search ..................... 435/2; 436/826, 177; 210/513, 514, 516, 782, 789; 422/101; 494/16–20, 37

[56] References Cited

U.S. PATENT DOCUMENTS

| | | | |
|---|---|---|---|
| 3,852,194 | 12/1974 | Zine, Jr. | 210/789 |
| 3,920,549 | 11/1975 | Gigliello et al. | 210/516 |
| 3,945,928 | 3/1976 | Ayres | 210/516 |
| 3,960,727 | 6/1976 | Hochstrasser | 210/359 |
| 4,101,422 | 7/1978 | Lamont et al. | 210/516 |
| 4,147,628 | 4/1979 | Bennett et al. | 210/516 |
| 4,153,739 | 5/1979 | Kessler | 427/2 |
| 4,190,535 | 2/1980 | Luderer et al. | 210/789 |
| 4,255,256 | 3/1981 | Ferrante et al. | 210/789 |
| 4,310,430 | 1/1982 | Ichikawa et al. | 210/782 |
| 4,350,593 | 9/1982 | Kessler | 210/516 |
| 4,417,981 | 11/1983 | Nugent | 210/516 |
| 4,435,293 | 3/1984 | Graham, Jr. et al. | 210/782 |
| 4,436,631 | 3/1984 | Graham, Jr. et al. | 210/782 |
| 4,457,782 | 7/1984 | Honda et al. | 210/516 |
| 4,487,700 | 12/1984 | Kanter | 210/789 |
| 4,534,798 | 8/1985 | Honda et al. | 210/510.1 |
| 4,640,785 | 2/1987 | Carroll et al. | 210/789 |
| 4,751,001 | 6/1988 | Saunders | 210/516 |

FOREIGN PATENT DOCUMENTS 1127537 7/1982 Canada .
0036168 9/1981 European Pat. Off. .

OTHER PUBLICATIONS

D. Rickwood; Iodinated Density Gradient Media, 1983, IRL Press.
Luderer, et al; Rapid, Quantitative Human Lymphocyte Separation and Purification in a Closed System, Molecular Immunology 16, (1979), pp. 621–624.
Nicholson, et al.; Comparison of Band T Cell Analyses on Fresh and Aged Blood; J of Immunological Methods, 73 (1984) 29–40.
Experimental Cell Research, Splinter, et al.

Primary Examiner—W. Gary Jones
Attorney, Agent, or Firm—Hoffman & Baron

[57] ABSTRACT

An assembly for separating lymphocytes and monocytes from granulocytes in a sample of unseparated whole blood. A water insoluble, thixotropic gel-like substance, which is chemically inert to blood constituents is provided in a container. A fluid capable of altering blood cell densities and diameters is positioned above the surface of the water-insoluble thixotropic gel-like substance. Means for preventing the absorption of water by the thixotropic gel-like substance from the fluid and/or the sample of unseparated whole blood prior to separation are provided to substantially eliminate the influence of water absorption on the cell separation performance characteristics of said thixotropic gel-like substance. A method for separating lymphocytes and monocytes from granulocytes which inhibits the apparent shift of the buoyant density of the granulocytes and which substantially eliminates the influence of water absorption on the cell separation performance characteristics of the thixotropic gel-like substance is also disclosed.

9 Claims, 1 Drawing Sheet

U.S. Patent
Jul. 4, 1989
4,844,818
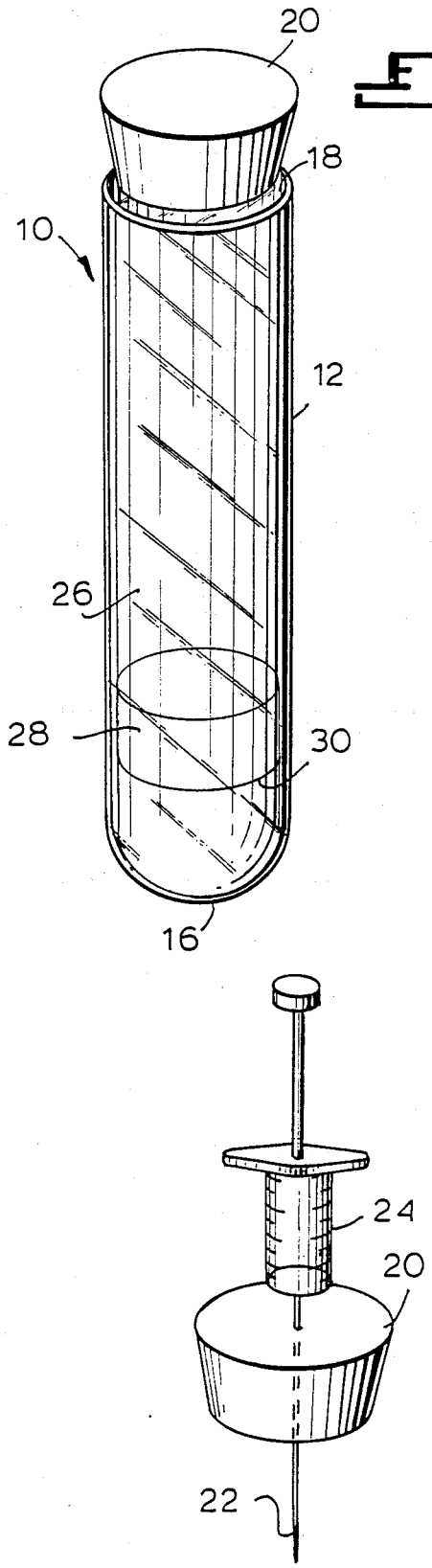
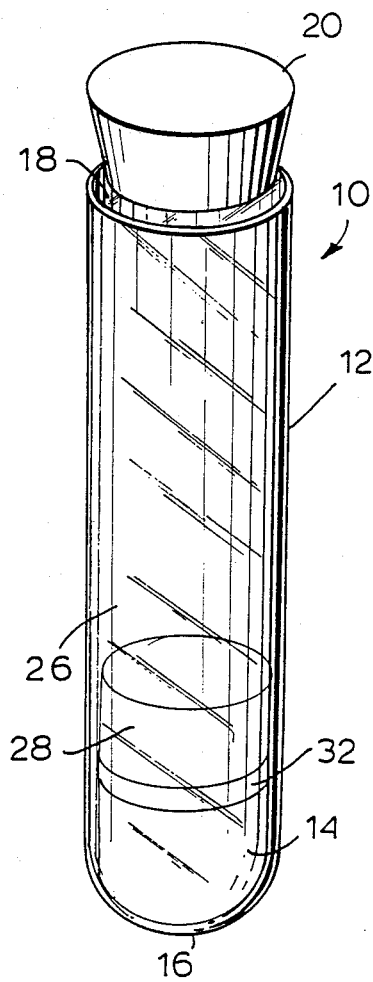

METHOD FOR SEPARATING THE CELLULAR COMPONENTS OF BLOOD SAMPLES

BACKGROUND OF THE INVENTION

The present invention relates generally to the separation of the cellular components of blood for performing diagnostic assays on certain blood cells, such as, lymphocytes. More specifically, the present invention relates to a blood cell separation method which substantially overcomes the problems associated with aging or aged blood, such as, the contamination of the blood cells to be analyzed.

Lymphocytes play a major part in the body's immune system. They are harvested and used in a major part of the research activity directed at defining the chemistry and physiology of immune mechanisms. For example, they comprise an important part of cancer and autoimmune disease research and are fundamental to monoclonal antibody technology. In the most basic sense, lymphocytes are white blood cells which are vital in the bodies defense against infection.

Because of the significance attributed to white blood cells and, particularly, lymphocytes, isolation of lymphocytes from human blood is clinically necessary for a variety of diagnostic assays. Included among such assays are functional assays, paternity testing and tissue typing. Furthermore, an assessment of immune competency can be accomplished through analysis of lymphocyte sub-types and ratios. This, in turn, is significant in the diagnosis of AIDS and, is prognostic in many other chronic and often terminal infections. These cellular assays are also utilized to monitor immune regulating drugs employed in cancer therapy. Additionally, an accurate measure of white blood cells, especially lymphocytes, is critical for histocompatibility determinations. Furthermore, an analysis of lymphocyte function, where the type and level of medication needed for immuno-suppression must be determined, is also vitally critical.

In order to analyze and test a certain type of blood cell, the particular cell, usually a lymphocyte, must be separated from other undesirable cells and then isolated for analysis. Blood cells can be separated and grouped according to density. It is the separation and isolation of lymphocytes from other cell types that have troubled the skilled artisan.

Generally, after the blood specimen is extracted from the patient and the specimen is caused to sit in vitro. the blood cells undergo a change in size and density, which complicates cellular separation according to density. In particular, once blood is drawn, the samples almost instantaneously begin a degradation process wherein the more fragile granulocytes rapidly undergo a change in size and density relative to other cellular components. As a result of the degradation, the granulocytes begin to migrate into the density population of lymphocytes and monocytes. This unwanted migration complicates the density separation of lymphocytes and monocytes. The problem only becomes compounded as the time span between draw and separation is further increased. That is, as the time between blood extraction and cellular separation increases, the lymphocytes population becomes increasingly contaminated with unwanted granulocytes. The result is that an accurate diagnostic assay of lymphocytes cannot be performed, since in the lymphocyte and monocyte population there are also unwanted granulocytes.

More particularly, it has been discovered through observation of a variety of normal and abnormal blood samples that there exists a wide variability in density of cells within a given cell type density population. In fact, mathematical consideration of the density profile of blood cell samples moving under theoretical conditions at sedimentation velocity through plasma would show a Gaussian distribution of each cell type over its density population range, with granulocytes overlapping trailing erythrocytes, lymphocytes overlapping trailing granulocytes, and monocytes overlapping trailing lymphocytes.

There are several ways in which cell density overlapping could be expected to increase. In vitro aging is one way in which overlapping of cell types occurs. Since typical cell densities are averages of many individuals, one would expect that samples on the extremes of normal distribution would show significant overlap. Certainly, pathologic examples would be expected to change cell population overlap and, in fact, do shift whole populations. These conditions can be expected to have a significant impact on variability in separation performance.

The mechanism responsible for density and volume shift of blood cells has been studied extensively. It is founded in three principal aspects of transport through cell membranes, namely, diffusion, facilitated transport, and active transport. Those transport systems are complex with various independent pathways which may be activated or blocked by different drugs. The $Na^+K^+$ pump is one such transport system.

A shift in osmolarity of the cell environment leads to the transport of ions into or out of the cell resulting in an obligatory change in water volume. This change in water volume constitutes the primary influence on cell size and density change. A detailed description of cell volume regulation is provided in "Biochimica Et Biophysica Acta," 774 (1984), pages 159–168, Elsevier Science Publishers Bv. In Chapter 7 of a publication by IRL Press, "Iodinated Density Gradient Media," edited by Dr. D. Rickwood, there is an extensive description of the technology and methods of density gradient liquid cell separation. It is shown there that a 10% increase in osmolarity will theoretically cause a 2.2% decrease in cell radius, with a concomitant 0.4% increase in cell density. Dr. Rickwood describes the use of Nycodenz ® and NaCl to control separation media density and osmolarity independently. Nycodenz ® is the trademark name for a density gradient medium marketed by Accurate Chemical and Scientific Corporation, Westbury, N.Y., having a molecular weight of 821 and a density of 2.1 g/ml. The chemical systematic name therefor is N,N'-Bis(2,3-dihydroxypropyl)-5-[N-(2,3-dihydroxypropyl)acetamido]-2,4,6-triiodoisophthalamide. The use of this medium to separate monocytes from lymphocytes is described, as well as the change in purity of monocytes as osmolarity is increased. A sedimentation gradient was used.

In the separation of cells utilizing liquid gradient media, three types of gradients are used. The first is a sedimentation gradient. Because of variations in sedimentation rates, in a given time one group of cells to be separated collects at the bottom of the tube while the second remains in the supernatant liquid. The second and third separation types are buoyant density gradients. Of these, the first is a discontinuous gradient. The sample is laid on top of the gradient. After sedimentation, one group of cells sits on top of the gradient liquid and the other in or beneath the density gradient. The second buoyant density gradient is called a continuous gradient. In this medium centrifugation causes the large molecules in the medium to move toward the bottom of the medium causing a continuous density gradient. Cells in this medium take up positions in the gradient according to their densities. Here one would expect density population overlap as described above and, as such, it is cellular separation employing a continuous gradient that constitutes the primary area of concern herein.

It has been discovered that the mechanism of gel separation is fundamentally different from conventional buoyant density separation. Thus, in the former, the gel is displaced from the bottom of the tube under centrifugal force by the mass of red cells which, when compacted, approaches a density of 1.09 g/cc. The gel, having a density of about 1.055–1.080 g/cc, is moved up the tube by buoyant force as the packed cell mass grows. The gel finally settles at a position where the suspension of cells approximates the density of the gel. That is, at a level where the combination of red cells, white cells, and plasma exhibits a density equal to, or substantially equivalent to, that of the gel.

At that equilibrium position the elongated gel mass is supported from below through the buoyant force of the mass of red cells. The suspension of cells at the top of the gel mass is less dense than the gel mass. This circumstance results in compression of the gel due to its weight under centrifugation. This compression forces the gel inwardly toward the center of the tube such that the mass assumes a configuration analogous to that of an hourglass. The rate at which the gel mass contracts or closes and the extent thereof is governed by the velocity of the cell gradient.

When sealing of the gel occurs, the stream of cells is attenuated, frequently with a thin stream of cells trapped in the gel mass, thereby forming, in essence, a marble. Plasma trapped underneath the gel tends to form a bubble as the cells compact below the gel and, if of sufficient size, will force its way up through the gel and produce a "hot lava pattern" on the surface of the gel. The gel then settles to replace the space left by the plasma.

One can mathematically approximate the conditions under which gel closure may occur; i.e., the conditions under which the buoyant forces of the cell gradient fall below the buoyant forces compressing the gel. Naturally, at equilibrium those forces are equal. If the fact that the system is acting over a gradient is ignored, the concept can be simplified. Thus, in so doing the sum of the products of the densities and percent volumes of the phases present can then be equated. Red cells have a nominal density of about 1.10 g/cc, white cells a density of about 1.075 g/cc, plasma a density of about 1.027 g/cc, and the gel a density in the range of about 1.055–1.080 g/cc. Two boundary conditions, one being for all white cells and the second being for all red cells, can be defined utilizing the above density values for the white and red blood cells, and arbitrarily choosing a density value of 1.065 g/cc for the gel. Accordingly:

| For only plasma and white cells: | $1.075(x) +$ |
|---|---|
| | $1.027 (1 - x) =$ |
| | $1.065 (1)$ |
| Where $x =$ % white cells $=$ | $(1.065 - 1.027) -$ |
| | $(1.075 - 1.027) =$ |
| | $\sim 0.79 = \sim 79\%$ white cells |
| For only plasma and red cells: | $1.10(x) +$ |
| | $1.027(1 - x) =$ |
| | $1.065(1)$ |
| Where $x =$ % red cells $=$ | $(1.065 - 1.027) -$ |
| | $(1.10 - 1.027) =$ |
| | $\sim 0.52 = \sim 52\%$ red cells |

Therefore, where a gel having a density of about 1.065 g/cc is employed, that gel will close on a cell suspension stream having a packed cell volume of about 50–80% in plasma, depending upon the mix of cells in the suspension. Obviously, a change in gel density will alter the boundary conditions.

An equation can also be developed to mathematically approximate the terminal velocity of a spherical particle moving under gravitational forces in a viscous liquid. The equation is operative only for single particles, however. Such an equation indicates that the velocity is a direct function of the density difference between the particle and the medium, a direct function of the square of the particle diameter, and an inverse function of the viscosity of the medium. Nevertheless, if this equation were to be applied to each cell type, the predicted result would be found to be somewhat opposite to the sequence occurring in actual separation of the phases. Thus, in the actual separation process the red cells appear to be first.

This phenomenon has been explained in the observation that the suspension of cells is so dense that mass cell streaming occurs with many red cells acting in mass with the equivalent diameter of the mass. It has been deemed likely that the red cells are first and last. That is, first because of a clumping and mass effect, and last because, as the cell suspension thins out during the separation, the individual cells move in accordance with the above equation such that the smallest cells arrive last. Hence, the front end of the cell suspension gradient moves under different influences than the trailing end thereof. Consequently, red cell contamination must be expected.

As the suspended cells approach the packed cell mass, the larger cells, which inherently move more rapidly than the smaller cells, begin to slow down due to the increasing density of the cell suspension. At a red cell concentration of about 60%, the density of the suspension approaches that of lymphocytes. Such a stream is sufficiently dense to support the gel opening, so white cells can be expected to slow down or even reverse direction, according to their densities, while still in a position above the gel and before the gel closes. Large numbers of red cells traveling downward at this stage of the separation process can be expected to pile up onto those white cells, thereby tending to oppose this action. This behavior may also explain, at least in part, some of the red cell contamination inasmuch as the white cells would, in turn, hold up the red cells. That is, the cells would begin to form layers according to the densities of the individual phases. Accordingly, in this sense the concentrated cell suspension begins to act as its own density separation gradient. The gel closes before equilibrium can be reached, but not before substantial density separation occurs.

When the density of the gel is increased, it can be expected to position itself lower in the tube, resulting in closure occurring sooner because of increased compression forces. This action is evidenced through the greater yield of cells as the density of the gel is increased. To illustrate, yields can be as low as 15-10% with a gel having density of 1.055 g/cc, but at 70-80% with a gel having a density of 1.08 g/cc. This advantage in yield can be lost where high purity of phase separation is desired, since the purity of the separated lymphocytes acts in reverse. Therefore, an optimum choice must be made between the two parameters. And in view of the above discussion, it is believed evident that applications demanding that the purity of the majority of samples be above 90% cannot be satisfied by varying only the physical properties of the gel.

Once the gel is sealed, the individual cells do not have sufficient density to displace the gel. Hence, as the cells move out of the plasma (density $\sim 1.027$ g/cc) and into the gel (for a chosen density $\sim 1.065$ g/cc), the relative density of the cell becomes negligible. The viscosity of the gel, being about 100,000 times that of plasma, further reduces cell velocity. Accordingly, a cell that travels two inches in plasma in a few minutes would require several days to sink to the depth of its own diameter into the gel. Stated another way, the gel comprises a door which closes, thereby leaving cells above it available for removal. Such cells constitute a lymphocyte-rich mixture of red and white cells.

Unlike conventional liquid density separation media, the gel medium does not act on individual cells in a buoyant density separation but, instead, assumes a position in the tube based upon the average buoyant density of a changing cell gradient in suspension; in essence acting as a door closing on a sedimentation gradient. Both because of the relative velocities of the cell types and the buoyant density effect of the cells themselves, the cells resting upon the top of the gel are lymphocyte-rich. Red cell contamination can be removed through lysing. Purification requires the addition of chemical agents to supplement the separation activity of the gel.

Inasmuch as individual cells do not reach buoyant density equilibrium, it is believed that cell diameter may exert a significant influence on the gel medium separation because of the diameter squared parameter in the above-discussed velocity equation. However, since the cell mass and the concentrated cell suspension are in motion, it is difficult to judge when velocity effects are replaced by buoyant density effects. Furthermore, assessment of the effect of red cell capturing, which prevents white cells from rising against the stream of descending red cells, is difficult. It is known that aging causes an increase in the diameter of cells, especially granulocytes, and that a forced reduction in cell size significantly improves the separation of aged blood samples. Hence, aging effects can effect changes in diameter five times greater than a change in density; density decreasing as the cell becomes larger. For example, a 2.2% change in diameter will result in a 5% change in cell sedimentation velocity.

When diameters of typical blood cells are reviewed, it will be observed that the granulocyte range falls within the lymphocyte range and the monocytes overlap the high end of the granulocyte range. The diameters of red cells are about equivalent to those of the smallest lymphocytes. Hence, there is considerable overlapping in the ranges of cell diameters. Consequently, the fact that a reasonably substantial separation occurs indicates that, because of the near coincidence of cell diameters, the densities of the cells, wherein there is much less overlap, must play a very significant role in the gel separation process. Therefore, it appears evident that velocity controls sedimentation profiles and constitutes a primary initial mechanism of the separation process, whereas during the latter portion of the separation process, i.e., when the cell concentration gradient is high and still above the gel closure position, density comprises the more dominant separation mechanism. Where a cell suspension is composed predominantly of red cells, it becomes its own separation gradient medium.

One known way to separate blood cells according to density is by employing an ionic density separation medium. The ionic character of this medium is said to correct the density changes associated with aged or aging blood. Among the known ionic density liquid separation media, Ficoll-Paque ® appears to be the most effective, since it is believed to oppose a natural reduction in cell component density. Ficoll-Paque ® is a Newtonian liquid having a specific gravity of 1.077 g/cc and is marketed by Pharmacia Fine Chemicals AB, Uppsala, Sweden.

A typical method of isolating mononuclear cells, such as, lymphocytes and monocytes, from blood specimens, employing Ficoll-Paque ® as an ionic density medium includes the following steps:

dispensing a pre-determined amount of Ficoll-Paque ® into the bottom of a test tube;

pipetting a sample of whole or diluted blood onto the Ficoll-Paque ®;

centrifuging the blood sample and Ficoll-Paque ® for about 30-40 minutes at about 400-500 g's; and pipetting the lymphocytes and monocytes off of the Ficol-Paque ® phase.

However, it has been discovered that this method can be improved upon for a variety of reasons. First, if during the initial pipetting of the blood sample onto the Ficoll-Paque ® liquid, white cells are accidentally deployed below the surface of that liquid, the reduced specific gravity of the Ficoll-Paque ® is inadequate to separate the lymphocytes and monocytes.

Second, if during centrifugation, lighter phases in the blood are carried into the Ficoll-Paque ® medium, they may not ascend therethrough because of the low buoyant force generated by the 400-500 G's.

Third, centrifugation forces greater than about 400-500 G's cannot be employed because Ficoll-Paque ® liquid is somewhat water soluble and, greater centrifugation speeds enhance the solubility thereof in blood, thereby leading to a reduction in its specific gravity. Stated another way, the water component in a diluted blood sample tends to dilute the Ficoll-Paque ® density medium which changes its density and prevents good separation.

Fourth, upon completion of centrifugation, withdrawal of the lymphocytes and monocytes from atop the Ficoll-Paque ® fluid must be carried out with great care because of the Newtonian character of the fluid.

Finally, since this separation technique requires, at minimum, between one (1) and two (2) hours for completion, a more time effective technique is highly desirable.

In order to prevent surface contact between the blood sample and the liquid density medium when the blood sample is pipetted into the liquid density medium, partition devices have been employed. Such devices repress the liquid density medium below the partition to prevent interaction between the blood sample and the liquid density medium until centrifuging occurs. Partition devices are known to be either porous or impermeable.

The impermeable partitions further require a mechanism which automatically unseals the partition upon centrifuging. These partitions are generally disclosed as being fabricated from plastics, elastomers, foams and thixotropic gels.

While these partition devices offer an adequate solution to one of the problems associated with cellular separation utilizing Newtonian liquids such as Ficoll-Paque ®, other alternatives were still sought towards further improvement.

Accordingly, another cellular separation technique employs a Newtonian gel density separation medium. These gels must typically be used in association with fillers. However, little or no fillers are required where the Newtonian gels are fabricated from high molecular weight resins. In this instance, appropriate densities can be attained without use of fillers, since a high viscosity liquid or gel is a natural result of polymerization. These type of gels without fillers are essentially hydrophobic and, as such, do not require separation from aqueous reagents used in cooperation with the selected density medium. A more detailed discussion of these reagents will appear hereinafter.

Thus, while it appears that the hydrophobicity of Newtonian gels would make them perfect candidates for density medium in cellular separation, they actually prove to be unsatisfactory as they cannot be used as a barrier for blood samples that have to be shipped, because of their characteristic instability.

When Newtonian gels are used along with fillers, the resulting gel is unsatisfactory since by definition there are insufficient bonding sites to hold the gel together. Furthermore, these fillers tend to absorb water which is detrimental for reasons which will be discussed hereinafter.

Still a more preferred technique for cellular separation is one which employs a thixotropic gel as a density medium.

For instance, U.S. Pat. No. 3,852,194 provides a general description of a process for separating lighter phases present in blood samples from heavier phases therein by means of a thixotropic, gel-like material having a specific gravity intermediate that of the phases to be separated. The gel and blood sample are centrifuged together and, during that operation, the gel flows sufficiently to form a barrier between the phases to be separated. The barrier allows the phase resting thereupon to be removed utilizing conventional laboratory techniques.

The patent suggests the utility of a wide variety of gel-like substances; three criteria therefor being cited as required attributes for those materials are as follows:
  (a) a specific gravity intermediate to the phases desired to be separated;
  (b) chemical inertness with respect to the phases desired to be separated; and
  (c) essentially non-flowable (semi-rigid) when at rest.

Similarly, U.S. Pat. No. 3,920,549 discloses a modification of, and an improvement upon the process of Pat. No. 3,852,194. The improvement involves the use of a solid element having a specific gravity greater than that of the gel-like substance. During centrifugation, the solid element, termed an "energizer", impacts upon the gel, which is commonly placed in the bottom of a blood collection tube, and thereby facilitates the upward movement of the gel along the walls of the tube. In so doing, the energizer hastens the separation of the blood fractions and enables a cleaner separation between the phases.

Analogously, U.S. Pat. No. 4,190,535 is explicitly directed to means for extracting lymphocytes, monocytes, and platelets from anticoagulated blood. Three basic process steps are involved:
  (1) a water-insoluble, thixotropic gel-like substance that is chemically inert to blood components and exhibits a specific gravity between about 1.065–1.077 g/cc is placed into a sample of anticoagulated blood;
  (2) the gel-blood sample is centrifuged at a force of at least 1200 G's for a sufficient length of time to cause the gel-like substance to form a barrier between the heavier blood cells and the plasma, platelets, lymphocytes, and monocytes; and, thereafter,
  (3) the plasma, platelets, lymphocytes, and monocytes are withdrawn from atop the barrier.

By utilizing a thixotropic, non-Newtonian, water-insoluble gel-like substance capable of forming a barrier at centrifugation forces of in excess of 1200 G's, the method disclosed in U.S. Pat. No. 4,190,535 provides a faster separation process and a more complete separation than possible with the Ficoll-Paque ® liquid.

The advantageous results attained by using a thixotropic gel are basically ascribed to the fact that the gel is only moveable under agitation, which in the present context, most often includes centrifugalization. Accordingly, the whole or diluted blood specimen can be poured into a tube along with the thixotropic gel without any interaction occurring prior to centrifuging due to the hydrophobicity of said gel. This characteristic alone is evidence of the superiority of thixotropic gels. Additionally, with thixotropic gels high centrifugal speeds may be employed and the centrifugalization may occur over a significantly reduced time period, since this type of gel will not separate into components or allow dilution with the aqueous phase during centrifuging. As a matter of fact, centrifuge speeds in the neighborhood of 1200 G's can be used as opposed to speeds of 400 G's for ionic liquid media such as Ficoll-Paque ® Moreover, centrifuge time is reduced from between 30–40 minutes (Ficoll-Paque ®) to about 10 minutes (thixotropic gels).

Thixotropic gels are essentially prepared from oils and resins which typically contain particle fillers. Thus, while thixotropic gels are an improvement over ionic liquids and Newtonian gels, the presence of water in these gels due to the filler particles has a significant effect in altering the number of binding sites and, thus, the viscosity of the gels. Such alterations in the viscosity of the gels can affect the separation performance of the product after substantial periods of storage. Moreover, thixotropic gels typically have a very low osmolarity and fail to correct the shifting of cell densities.

It is possible, however, to use thixotropic gel in cooperation with chemical reagents that will alter the osmolarity of the blood plasma to change the cell diameters and cell density.

More specifically, it is possible to alter the osmolarity of the plasma through the use of chemical reagents which change cell diameters and cell densities. Thus, the cells of a given cell type can be moved toward the center of population of that cell type, thereby reducing the range of density. That movement has the effect of thinning the extent of overlapping of the cell populations. For example, the larger lymphocytes which lead the lymphocyte sedimentation profile can be drawn back toward the lymphocyte center of population. The small, trailing granulocytes will not be significantly influenced since such a hyper-osmotic chemical treatment is less effective on cells of relatively small density. At the same time, however, the density of large granulocytes will be so modified as to move them toward the center of the granulocyte population. This latter action becomes important at the conclusion of the separation process where buoyant density effects would otherwise cause the large granulocytes to be forced upward out of the mass of red cells. The overall result is that lymphocytes are held back and granulocytes facilitated down the tube during the separation process through the use of a density/size adjusting reagent. In sum, because the cell types are given a greater separation distance, the gel can close with fewer granulocytes trapped in the lymphocyte population, thereby leading to improved purity.

In particular, U.S. Patent Application Serial No. 923,909 generally describes a fresh or aged anticoagulated blood sample being mixed with a hypertonic fluid containing a low molecular weight organic and/or inorganic ionic substance and/or the isotonic or hypertonic fluid containing a high molecular weight substance having molecules which may contain a lipophilic substituent, contact between said blood sample and said fluid being maintained for more than about 1 minute.

In general, this method is designed to maintain the purity or quality of lymphocytes and monocytes from samples of anticoagulated human blood via the use of a gel separation medium by inhibiting the apparent shift in the buoyant density of the granulocytic white blood cells.

The foregoing is but one example of a chemical reagent used to change cell densities and cell diameters in plasma. Regardless, the use of most aqueous stabilizing reagents in direct contact with thixotropic gel offers the potential for performance degradation, it also offers the possibility of a changing appearance of the gel which can present a cosmetic problem. When a gel is in contact with an aqueous reagent or media for a period of time, the water swells the filler particles to a size where they become visible as a white layer of gel at the aqueous interface. As time elapses this whitening proceeds through the entire gel mass. If the mass of water absorbed is significant there is a reduction in gel density.

It has also been discovered that the addition of a cell culture media when added to the blood sample immediately upon extraction provides an, in vivo, type environment which minimizes cellular degradation. In this instance, a 0.5:1 dilution of cell culture media such as RPMI 1640 to whole blood will allow good separations over an extended period of time after blood drawing when used with a non-ionic density separation media. Without the stabilizing reagent, increased contamination is observable within 15 to 30 minutes. Increasing the dilution ratio of stabilizing reagent to whole blood increases the effective time between blood drawing and separation of cells for good separation performance.

The addition of stabilizing reagent to a 1:1 dilution with whole blood will significantly extend the time before centrifugation is necessary for good performance. The amount of stabilizing reagent that will allow a hiatus period of 18-24 hours before separation, is ideal. This would make it unnecessary for the physician to centrifuge the collection tube containing the blood specimen, density medium and stabilizing reagent, before shipping to a reference laboratory. However, it appears on initial testing that dilutions on the order of 2:1 and 3:1 perform less well after 24 hours than a 1:1 dilution. The reason for this is not yet known.

It is also observed that settling of cells in an upright tube tends to separate the cells from the stabilizing liquid, leading to poor results. It is important to realize that at least 3-4 ml. of whole blood are essential to have sufficient cells to do the required analysis. This limits the amount of stabilizing reagent that can be practically utilized in an acceptable gel separation tube.

It is therefore an object of the present invention to provide a method for the separation of various blood cells which would overcome those problems associated with aged or aging blood.

It is a further object of the present invention to provide a method for separating lymphocytes from a blood sample while substantially eliminating the overlapping of cells other than lymphocytes into the lymphocytes population.

It is another object of the present invention to provide a method for separating lymphocytes from a blood sample while substantially eliminating the overlap of other cells into the lymphocyte population so that the lymphocytes can undergo diagnostic assays.

It is yet a further object of the present invention to substantially prevent the change in buoyant density of certain blood cells after a blood sample has been extracted from a human being.

It is yet another object of the present invention to provide a method of isolating mononuclear cells, such as, lymphocytes and monocytes from blood specimens which overcomes those shortcomings associated with those methods utilizing ionic density media.

It is still another object of the present invention to provide a more efficient method for blood cell separation or isolation from the perspectives of time and centrifuge speeds.

It is still a further object of the present invention to provide a method for blood cell separation employing a thixotropic gel while avoiding performance degradation and overcoming those cosmetic problems discussed hereinabove.

It is another object of the present invention to provide a means for eliminating the transfer of water into a non-ionic density gel media which would otherwise cause a negative change in separation performance.

SUMMARY OF THE INVENTION

Broadly contemplated, the foregoing objects and advantages are accomplished by providing an assembly for separating lymphocytes and monocytes from granulocytes in a sample of unseparated whole blood and inhibiting any apparent shift in the buoyant density and/or restoring any loss in buoyant density of the granulocytes which comprises:
(a) a container having an open end and a closed end;
(b) a water insoluble, thixotropic gel-like substance, which is chemically inert to blood constituents, positioned adjacent said closed end;
(c) a chemical reagent in fluid communication with the thixotropic gel-like substance, said chemical reagent being provided to alter the osmolarity of the blood, thereby changing cell diameters and cell densities of the granulocytes;
(d) a free space initially adjacent and above the chemical reagent, the free space of sufficient volume to contain the sample of unseparated whole blood; and (e) means for preventing the absorption of water by the thixotropic gel-like substance from the chemical reagent and/or the sample of unseparated whole blood prior to separating the lymphocytes and monocytes from the granulocytes so as to substantially eliminate the influence of water absorption on the cell separation performance characteristics of the thixotropic gel-like substance.

In accordance with another aspect of the present invention, also provided is a method for separating lymphocytes and monocytes from granulocytes in a sample of unseparated whole blood wherein an apparent shift in the buoyant density of the granulocytes is inhibited and any loss in buoyant density of the granulocytes is restored. The method comprises the following steps:

(a) mixing the sample of blood with a fluid selected from the group consisting of a hypertonic fluid containing a low molecular weight organic ionic substance which is essentially chemially compatible with the blood cells, a hypertonic fluid containing a lower molecular weight inorgaic ionic substance which is essentially chemically compatible with the blood cells, and a culture medium for blood cells, and combinations thereof;

(b) introducing a water insoluble, thixotropic gel-like substance, which is chemically inert to blood constituents, into the mixture resulting from step (a);

(c) providing means for preventing the absorption of water by the thixotropic gel-like substance from the fluid and/or the sample of unseparated whole blood in the mixture resulting from step (b) prior to separating the lymphocytes and monocytes from the granulocytes so as to substantially eliminate the influence of water absorption on the cell separation performance characteristics of the thixotropic gel-like substance;

(d) centrifuging the blood-fluid-gel mixture resulting from step (c) at a force and for a sufficient length of time to cause the gel-like substance to flow sufficiently to form a barrier between the lymphocytes and monocytes and the granulocytes; and (e) removing the lymphocytes and monocytes from atop the barrier.

In one embodiment of the present invention the means for preventing the absorption of water by the thixotropic gel-like substance from the chemical reagent and/or the sample of unseparated whole blood is provided by fabricating the thixotropic gel-like substance from an organic resin which allows high density and high viscosity polymers to form, so that the thixotropic gel-like substance is substantially devoid of organic fillers which can absorb the water.

In an alternate embodiment of the present invention the means for preventing the absorption of water by the thixotropic gel-like substance from the chemical reagent and/or the sample of unseparated whole blood is provided by presaturating the thixotropic gel-like substance with water during manufacture and/or curing of the thixotropic gel-like substance.

In another embodiment of the present invention, the means for preventing the absorption of water by the thixotropic gel-like substance from the chemical reagent and/or the sample of unseparated whole blood is provided by interposing a barrier between the thixotropic gel-like substance and the chemical reagent and/or the sample of unseparated whole blood. The barrier can include a thixotropic gel-like substance which is devoid of any density medium property used in combination with a thixotropic gel-like substance having density medium properties. The barrier can also include a porous foam used in cooperation with a thixotropic gel-like substance and a Newtonian gel-like substance. Finally, the barrier can include a plastic or elastomeric partition.

In a preferred embodiment, the chemical reagent employed to alter the osmolarity of the blood can be one selected from the group consisting of a hypertonic fluid containing a low molecular weight organic ionic substance which is essentially chemically compatible with the blood cells, a hypertonic fluid containing a low molecular weight inorganic ionic substance which is essentially chemically compatible with the blood cells, an isotonic fluid containing a high molecular weight organic substance which is essentially chemically compatible with the blood cells, a culture medium for blood cells and combinations thereof.

The present invention provides an improved assembly and method for the separation of the cellular components of blood where a thixotropic gel-like substance is used as the separation media, since the adverse influence of water absorption on the cell separation performance characteristics of the thixotropic gel-like substance is substantially eliminated.

DESCRIPTION OF THE DRAWINGS

FIG. 1 is a perspective view of one embodiment of the assembly of the present invention;

FIG. 2 is a perspective view of another embodiment of the assembly of the present invention; and FIG. 3 is a perspective view of the closure means being pierced by a syringe for supplying a sample of blood into the vessel.

DESCRIPTION OF THE PREFERRED EMBODIMENTS

While the present invention primarily relates to the cellular separation of blood according to a technique employing a thixotropic gel as a density medium, one embodiment of the present invention relates to a technique employing a combination of gels as a density medium, such as, a combination of a thixotropic gel and a Newtonian gel.

Thixotropic gels of the kind used in the cellular separation of blood are generally described by A. A. Luderer, A. R. Zine, D. M. Hess, J. N. Henyan, and G. Odstrchel, "Rapid, Quantitative Human Lymphocyte Separation and Purification in a Closed System", *Molecular Immunolooy.* 16, pp. 621–624 (1979). Additionally, U.S. Pat. No. 4,190,535 describes suitable thixotropic gels and their preparation. Essentially, a water insoluble, thixotropic gel chemically inert to blood constituents can be formulated from a dimethyl polysiloxane and a precipitated methylated silica in which the methylation renders the material hydrophobic. The thixotropic gel preferably has a specific gravity of between about 1.055 to about 1.080 g/cm$^3$, and is optimally formed to have a specific gravity of about 1.077 g/cm$_3$ The cellular separation actually occurs in separator tubes in the manner which has been heretofor described. Thus, as illustrated in FIGS. 1 and 2 the assembly 10 can be aseptically prepared by depositing gel 14 on the bottom of a sterile, siliconized glass test tube 12 containing sufficient sodium heparin, for example, to act as an anti-coagulant followed by placing sterile polyester energizers in the center of the gel mass, as is described in U.S. Pat. No. 3,920,549. Other known anticoagulants, e.g., EDTA, may be employed with equal facility. The separator tubes are then evacuated. Because the plastic energizer possesses a specific gravity greater than the gel, centrifugation forces the energizer through the gel, displacing gel up the walls of the test tube. This action, while not mandatory for satisfactory tube performance, facilitates separation and gel seal formation.

The use of the closed system separator tube minimizes problems in the handling of the blood samples. Nevertheless, open tubes, such as those described in U.S. Pat. No. 4,190,535, are also operable. Also, other gel formulations have been found to perform in a similar manner. For example, gels modified from serum separation tube formulations, such as are described in U.S. Pat. Nos. 4,101,422 and 4,310,430, have demonstrated similar operability.

Thus, test tube 12 includes a closed end 66 and an open end 18. In a preferred embodiment, the closed system separator tube referred to above is fabricated with the aid of closure means 20 which is adapted to close open end 18 when the former is inserted over the latter so that open end 18 becomes vacuum sealed.

As illustrated in FIG. 3, closure means 20 is pierceable by a needle 22, such as one typically associated with a syringe 24 to supply a sample of blood within the free space 26 positioned above the chemical reagent 28 used to alter the osmolarity of the blood sample, as described hereinabove and immediately below. Of course, it is to be understood that the syringe 24 and needle 22 are also employed to extract a sample of blood from a patient.

As stated earlier, thixotropic gels are more successfully employed when used in cooperation with certain chemical reagents which will alter the osmolarity of the blood plasma to change cell diameters and cell density. Some of these chemical reagents have been discussed hereinabove and are generally disclosed in U.S. Pat. Application Ser. No. 923,909.

Similarly, a culture medium for blood cells can constitute the reagent for inhibiting a shift in the buoyant density of and/or to restore loss in the buoyant density of granulocytes.

These chemical reagents 28 are typically employed with the thixotropic gels 14 in the same container, such as, a test tube 12.

Cells in their natural environment live in a homeostatic system which provides for their normal growth. These cells in vitro tend to exhibit aging effects and eventually die due to the lack of such a system. Many types of cell media have been developed to support cell growth in vitro. Most typically, cells are separated and grown in a medium suspension of cells.

It has been found that the cell separation characteristics of whole blood can be preserved by adding a cell culture medium thereto. While it is believed that any cell culture medium for blood cells will give positive results, Roswell Park Memorial Institute medium and McCoy's medium were particularly effective. For example, when whole blood samples were diluted with amounts of those media varying about 20–50% by volume, the purities of the separations were generally better than those achieved with hypertonic salt solutions and salt solutions with Nycodenz ®. Thus, purity performance shifts from about 83% to about 93% have been observed.

J. K. A. Nicholson et al. in "Comparison of T and B Cell Analyses on Fresh and Aged Blood," *Journal of Immunological Methods,* 73, pp. 29–40 (1984) describe the dilution of whole blood samples with a cell culture medium, specifically noting the use of McCoy's 5a medium. However, there was no disclosure by the authors that the addition of cell culture medium imparted any beneficial effect in the separation of lymphocytes from granulocytes. That is to say, the authors simply indicated a routine dilution of blood samples with no recognition or even an intimation that a cell culture medium can be utilized in the mode of the present invention, namely, not only as a diluent but also as a preservative for whole blood. No mention whatever is made of its utility in improving the separation of lymphocytes and granulocytes in a blood sample employing a gel-like substance in the inventive separation process.

However, use of chemical reagents in cooperation with thixotropic gels results in performance degradation, as well as those cosmetic problems discussed previously.

These difficulties are ascribed to the fact that water is transferred from the reagents, typically in an aqueous solution, into the non-ionic density gel media when the reagents are in fluid communication with the gel media as illustrated by reference numeral 30 in FIG. 1. Water transfer is due in part to the hydrophilic nature of the organic fillers present in the organic resins used to fabricate the thixotropic gels. Thus, in one embodiment, the present invention employs a thixotropic gel fabricated from an oil or an organic resin, or an inorganic resin such as silicone, requiring a minimal amount or even no inorganic fillers, such as silica. More specifically, the thixotropic gel may be formed from a silicone oil, a butadiene resin, a polyester resin, or a butylene resin.

In another embodiment, the thixotropic gel to be used as a density medium can undergo modification or pre-treatment by pre-saturating the thixotropic gel with water during manufacture and/or during the curing period of the gel. Such pre-saturation can be accomplished by mixing water with the gel and letting the mixture stand until the water is sufficiently absorbed by the gel.

The result of such pre-saturation will render those changes with respect to both viscosity and density fixed and predictable at a relatively low level of change. By employing this pre-saturation step, the water present in the aqueous solution of chemical reagent which contacts the gel, in vitro, will not result in any additional transfer of water from the aqueous solution into the gel.

From a cosmetic point of view, there will be no apparent change in the appearance of the product as time elapses since the gel has already been saturated. Stated another way, any absorption of water by the fillers employed in the gel, which typically include silica particulate, and the associated visual whitening would have already occurred.

Another embodiment of the present invention, as illustrated in FIG. 2, employs a combination of differing thixotropic gels or a combination of thixotropic and Newtonian gels as the density medium. When two thixotropic gels are used, one has a lower density than the other. As a most preferred embodiment the density medium includes a combination of a thixotropic gel with density medium properties and a thixotropic gel without density medium properties. Water tends to follow the fillers or particles, such as silica, used to make the density medium. Leaving out such fillers or particles tends to make the gel hydrophobic, and it acts as a barrier. The barrier gel will be typically less dense than the gel separation medium. The barrier 32 resulting from this combination is stable while requiring only a minimal amount of hydrophobic gel.

Analogously, a stable hydrophobic barrier 32 can be produced by using a thixotropic gel and a Newtonian gel in cooperation with a porous material. As merely illustrative, porous materials of this type can include urethane foams and fibers, various filter materials, and plastic materials, such as polypropylene. The thus formed barrier 32 maintains its integrity during handling and storage, thereby maintaining the separation between the aqueous reagents 28 and the thixotropic gel 14.

In an alternative embodiment, the porous foam can contain the aqueous reagent 28, wherein the resulting arrangement would provide the Newtonian gel being held, as the barrier 32, between the thixotropic gel and the reagent saturated porous foam. Alternatively, a second quantity of the thixotropic gel can be employed as the barrier 32 holding the Newtonian gel in contact with the thixotropic gel. In this case, the amount of Newtonian gel required to form the hydrophobic barrier 32 is small relative to the substantially large amount of thixotropic gel 14 that would be required for stability.

In another embodiment of the present invention, a barrier 32 can be formed between the thixotropic gel 14 and the aqueous solution containing the chemical reagents 28 by using a plastic or elastomeric partition. These partitions would have channels therethrough (not shown) which are adapted to become opened during centrifugation thereby allowing passage of the required container contents. In other words, as opposed to a foam or filter-type barrier, a structure is molded which has channels. The structure keeps the aqueous reagent 28 or blood sample separated from the gel 14 and holds it in place until the separation device is spun, at which time the reagent or blood sample passes through the structure.

The channels which extend through the partitions and which become opened during centrifugation are formed during manufacture of the part, for example, as a honeycomb structure.

Accordingly, by modifying the structure of the thixotropic gel by pre-saturation or by minimizing the amount of fillers employed therein, or by interposing a barrier between the aqueous layer and the thixotropic gel density medium, the present invention overcomes those problems relating to water absorption by the thixotropic gel density medium.

It will be appreciated that, whereas the present invention is specifically directed to aged blood samples, the process is operable with fresh blood.

While preferred embodiments and several variations of the present invention are described in detail herein, it should be apparent that the disclosure and teachings of the present invention will suggest many alternative designs to those skilled in the art.

What is claimed is:

1. An assembly for separating lymphocytes and monocytes from granulocytes in a sample of unseparated whole blood and inhibiting any apparent shift in the buoyant density and restoring any loss in buoyant density of the granulocytes which comprises:
   (a) a container having an open end and a closed end;
   (b) a water insoluble, first thixotropic gel-like substance having density medium properties which is chemically inert to blood constituents, positioned adjacent said closed end;
   (c) a chemical reagent positioned adjacent said thixotropic gel-like substance, said chemical reagent being provided to alter the osmolarity of said blood, thereby changing cell diameters and cell densities of said granulocytes;
   (d) a free space initially adjacent and above said chemical reagent, said free space of sufficient volume to contain said sample of unseparated whole blood; and
   (e) means for preventing the absorption of water by said thixotropic gel-like substance from at least one of said chemical reagent and said sample of unseparated whole blood prior to separating said lymphocytes and monocytes from said granulocytes so as to substantially eliminate the influence of water absorption on the cell separation performance characteristics of said thixotropic gel-like substance, said means for preventing the absorption of water by said thixotropic gel-like substance including a barrier interposed between said thixotropic gel-like substance and at least one of said chemical reagent and said sample of unseparated whole blood, said barrier including a second thixotropic gel-like substance devoid of any density medium properties which is used in combination with the first thixotropic gel-like substance having density medium properties 2. An assembly for separating lymphocytes and monocytes from granulocytes in a sample of unseparated whole blood and inhibiting any apparent shift in the buoyant density and restroing any loss in buoyant density of the granulocytes which comprises:
   (a) a container having an open end and a closed end;
   (b) a water insoluble, thixotropic gel-like substance, which is chemically inert to blood consituents, positioned adjacent said closed end;
   (c) a chemical reagent positioned adjacent said thixotropic gel-like substance, said chemical reagent being provided to alter the osmolarity of said blood, thereby changing cell diameters and cell densities of said granulocytes;
   (d) a free space initially adjacent and above said chemical reagent, said free space of sufficient volume to contain said sample of unseparated whole blood; and
   (e) means for preventing the absorption of water by said thixotropic gel-like substance from at least one of said chemical reagent and said sample of unseparated whole blood prior to separating said lymphocytes and monocytes from said granulocytes so as to substantially eliminate the influence of water absorption on the cell separation performance characteristics of said thixotropic gel-like substance, said means for preventing the absorption of water by said thixotropic gel-like substance including a barrier interposed between said thixotropic gel-like substance and at least one of said chemical reagent and said sample of unseparated whole blood, said barrier including a porous material and a Newtonian gel-like substance used in cooperation with the thixotropic gel-like substance.

3. The assembly of claim 2 wherein said porous material is formed of at least one of urethane foams or fibers, plastic and polypropylene.

4. The assembly of claim 2 wherein said chemical reagent is contained within said porous material.

5. A method for separating lymphocytes and monocytes from granulocytes in a sample of unseparated whole blood wherein an apparent shift in the buoyant density of the granulocytes is inhibited and any loss in the buoyant density of the granulocytes is restored, said method comprising the steps of:
   (a) introducing a water insoluble first thixotropic gel-like substance having density medium properties into a vessel having an open end and a closed end, said thixotropic gel-like substance being positioned adjacent said closed end;
   (b) introducing a chemical reagent that is adapted to alter the osmolarity of said blood resulting in a change in cell diameters and cell densities of said granulocytes into said vessel;
   (c) providing within said vessel, means for preventing the absorption of water by said thixotropic gel-like substance from at least one of said chemical reagent and said sample of unseparated whole blood so as to substantially eliminate the influence of water absorption on the cell separation performance characteristics of said thixotropic gel-like substance;
   (d) introducing said sample of unseparated whole blood into said vessel; and
   (e) centrifuging said vessel at a force and for a sufficient length of time to cause said thixotropic gel-like substance to flow in order to form a barrier between said lymphocytes and monocytes, and the granulocytes, said means for preventing the absorption of water being provided by interposing a second barrier between said thixotropic gel-like substance and at least one of said chemical reagent and said sample of unseparated whole blood, said second barrier including a second thixotropic gel-like substance devoid of any desity medium properties which is used in combination with the first thixotropic gel-like substance having density medium properties.

6. A method for separating lymphocytes and monocytes from granulocytes in a sample of unseparated whole blood wherein an apparent shift in the buoyant density of the granulocytes is inhibited and any loss in the buoyant density of the granulocytes is restored, said method comprising the steps of:
   (a) introducing a water insoluble, thixotropic gel-like substance into a vessel having an open end and a closed end, said thixotropic gel-like substance being positioned adjacent said closed end;
   (b) introducing a chemical reagent that is adapted to alter the osmolarity of said blood resulting in a change in cell diameters and cell densities of said granulocytes into said vessel;
   (c) providing within said vessel, means for preventing the absorption of water by said thixotropic gel-like substance from at least one of said chemical reagent and said sample of unseparated whole blood so as to substantially eliminate the influence of water absorption on the cell separation performance characteristics of said thixotropic gel-like substance;
   (d) introducing said sample of unseparated whole blood into said vessel; and
   (e) centrifuging sai vessel at a force and for a sufficient length of time to cause said thixotropic gel-like substance to flow in order to form a barrier between said lymphocytes and monocytes, and the granulocytes, said means for preventing the absorption of water being provided by interposing a second barrier between said thixotropic gel-like substance and at least one of said chemical reagent and said sample of unseparated whole blood, said second barrier including a porous material and a Newtonian gel-like substance used in cooperation with the thixotropic gel-like substance.

7. The method of claim 6 wherein said porous material is formed of at least one of urethane foams or fibers, plastic and polypropylene.

8. The method of claim 6 wherein said chemical reagent is contained within said porous material.

9. A method for separating lymphocytes and monocytes from granulocytes in a sample of unseparated whole blood wherein an apparent shift in the buoyant density of the granulocytes is inhibited and any loss in the buoyant density of the granulocytes is restored, said method comprising the steps of:
   (a) introducing a water insoluble, thixotropic gel-like substance into a vessel having an open end and a closed end, said thixotropic gel-like substance being positioned adjacent said closed end;
   (b) introducing a chemical reagent that is adapted to alter the osmolarity of said blood resulting in a change in cell diameters and cell densities of said granulocytes into said vessel;
   (c) providing within said vessel, means for preventing the absorption of water by said thixotropic gel-like substance from at least one of said chemical reagent and said sample of unseparated whole blood so as to substantially eliminate the influence of water absorption on the cell separation performance characteristics of said thixotropic gel-like substance;
   (d) introducing said sample of unseparated whole blood into said vessel; and
   (e) centrifuging said vessel at a force and for a sufficient length of time to cause said thixotropic gel-like substance to flow in order to form a barrier between said lymphocytes and monocytes, and the granulocytes, said means for preventing the absorption of water being provided by interposing a second barrier between said thixotropic gel-like substance and at least one of said chemical reagent and said sample of unseparated whole blood, said second barrier including a plastic or elastomeric partition, said plastic or elastomeric partition further comprising channels extending therethrough, said channels being adapted to become opened to allow passage of a predetermined substance or substances through said second barrier.

* * * * *